(12) United States Patent
Norris

(10) Patent No.: US 11,591,563 B2
(45) Date of Patent: Feb. 28, 2023

(54) POST-SPORULATION MODIFICATION OF SPORES AND BIOLOGICAL INDICATOR

(71) Applicant: American Sterilizer Company, Mentor, OH (US)

(72) Inventor: Stephen Norris, Cleveland, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 16/938,052

(22) Filed: Jul. 24, 2020

(65) Prior Publication Data

US 2021/0024881 A1 Jan. 28, 2021

Related U.S. Application Data

(60) Provisional application No. 62/879,269, filed on Jul. 26, 2019.

(51) Int. Cl.
*C12N 3/00* (2006.01)

(52) U.S. Cl.
CPC ..................... *C12N 3/00* (2013.01)

(58) Field of Classification Search
CPC ..................................................... C12N 3/00
See application file for complete search history.

(56) References Cited

U.S. PATENT DOCUMENTS

| | | |
|---|---|---|
| 2013/0224757 A1 | 8/2013 | Bjoernvad et al. |
| 2014/0099657 A1 | 4/2014 | Buhr |
| 2014/0308733 A1 | 10/2014 | Nishiyama et al. |
| 2019/0002819 A1 | 1/2019 | Heffron |

FOREIGN PATENT DOCUMENTS

| | | | | |
|---|---|---|---|---|
| CN | 107475172 A | * | 12/2017 | ............... C12N 1/20 |
| CN | 107475172 A | | 12/2017 | |
| JP | 2826945 B2 | * | 11/1998 | |
| WO | 2008043368 A2 | | 4/2008 | |
| WO | 2018163094 A1 | | 9/2018 | |

OTHER PUBLICATIONS

Raguse, M., Fiebrandt, M., Stapelmann, K., Madela, K., Laue, M., Lackmann, J. W., . . . & Moeller, R. (2016). Improvement of biological indicators by uniformly distributing Bacillus subtilis spores in monolayers to evaluate enhanced spore decontamination technologies. Applied and environmental mi (Year: 2016).*
Beuchat, L. R., Pettigrew, C. A., Tremblay, M. E., Roselle, B. J., & Scouten, A. J. (2004). Lethality of chlorine, chlorine dioxide, and a commercial fruit and vegetable sanitizer to vegetative cells and spores of Bacillus cereus and spores of Bacillus thuringiensis. Journal of food protection, 67(8), (Year: 2004).*
Arun, A., Peters, N. T., Scornet, D., Peters, A. F., Mark Cock, J., & Coelho, S. M. (2013). Non-cell autonomous regulation of life cycle transitions in the model brown alga Ectocarpus. New Phytologist, 197(2), 503-510 (Year: 2013).*
Ababneh, Q. O., Tindall, A. J., & Herman, J. K. (2015). A secreted factor coordinates environmental quality with Bacillus development. Plos one, 10(12), e0144168 (Year: 2015).*
Otte, J. M., & Podolsky, D. K. (2004). Functional modulation of enterocytes by gram-positive and gram-negative microorganisms. American Journal of Physiology-Gastrointestinal and Liver Physiology, 286(4), G613-G626 (Year: 2004).*
Withers, H. L., & Nordström, K. (1998). Quorum-sensing acts at initiation of chromosomal replication in *Escherichia coli*. Proceedings of the National Academy of Sciences, 95(26), 15694-15699 (Year: 1998).*
Translation of Ikuo JP 2826945 B2 (Year: 1998).*
Luo CN-107475172-A machine translation (Year: 2017).*
Marina Raguse et al.; "Improvement of Biological Indicators by Uniformly Distributing Bacillus subtilis Spores in Monolayers To Evaluate Enhanced Spore Decontamination Technologies", Applied and Environmental Microbiology, vol. 82, No. 7, Jan. 22, 2016, pp. 2031-2038.
Milene B. Tavares et al.; "Bacillus subtilis Endospores at High Purity and Recovery Yields: Optimization of Growth Conditions and Purification Method", Current Microbiology, vol. 66, No. 3, Mar. 1, 2013, pp. 279-285.
Heather A Colburn et al.; "The effect of growth medium on B. anthracis Sterne spore carbohydrate content", Journal of Microbiological Methods, Elsevier, vol. 85, No. 3, Feb. 28, 2011, pp. 183-189.
PCT/US2020/043436; PCT International Search Report and Written Opinion of the International Searching Authority dated Sep. 29, 2020.

* cited by examiner

*Primary Examiner* — Louise W Humphrey
*Assistant Examiner* — Trevor L Kane
(74) *Attorney, Agent, or Firm* — Renner, Otto, Boisselle & Sklar, LLP

(57) ABSTRACT

A liquid sporulation method is described. A liquid culture is prepared by adding bacterial cells to a sporulation broth. The liquid culture is incubated. Spores are harvested from the incubated liquid culture by separating the spores from a culture supernatant. In some embodiments, the harvested spores are suspended in an aqueous medium to form a spore suspension. At least a portion of the culture supernatant is combined with the spore suspension.

23 Claims, 2 Drawing Sheets

POST-SPORULATION MODIFICATION OF SPORES AND BIOLOGICAL INDICATOR

RELATED APPLICATION DATA

This application claims the benefit of U.S. Provisional Patent Application No. 62/879,269, filed Jul. 26, 2019, the disclosure of which is incorporated herein by reference in its entirety.

TECHNICAL FIELD

The present disclosure relates to a method of producing spores, and more specifically to the post-sporulation modification of spores and biological indicators including the same.

BACKGROUND

In the health care industry as well as in many other commercial and industrial applications, it is often necessary to monitor the effectiveness of processes used to sterilize equipment such as medical and non-medical devices, instruments and other articles and materials. A biological indicator including spores can be included in the batch of articles to be sterilized to assay the lethality of the sterilization process. Such a biological indicator can also be used to validate the effectiveness of sterilization equipment and sterilization cycles used in such equipment. Following the sterilization process, the biological indicator can be exposed to a growth media or other detection media for the purpose of determining the viability of the spores.

Spores are a highly resistant, dormant cells formed by some types of bacteria. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore-specific layers. The mother cell then disintegrates, releasing the mature dormant spore which requires neither nutrients, water, nor air for survival and is protected against a variety of trauma, including extremes of temperature, radiation, and chemical assault. The resistance of the spore to such trauma is typically higher than the vegetative cell variant. One type of method for producing spores used in connection with a biological indicator is a plate-based culture method in which bacterial cells cultured using a series of sets of Petri plates to produce spores that meet the desired product's acceptance criteria.

In some embodiments, viability of the spores subsequent to the sterilization process is determined by germination of viable spores into vegetative cells, where spore outgrowth may be identified via an associated color change of media within the biological indicator. However, traditional growth-dependent biological indicators require a significant time investment as even an unexposed positive control biological indicator can take several hours of incubation to produce sufficient acid to induce a color change. In other embodiments, viability of the spores subsequent to the sterilization process is determined using a proxy indicator of spore survival, where the proxy is an enzymatic hydrolysis of a non-fluorescent substrate into a fluorescent moiety from enzymes of the spores. However, growth or nascent enzyme production by spores can lack the rapidity needed for verifying the sterilization process in many health care settings.

SUMMARY OF THE INVENTION

The application relates to post-sporulation modification of spores produced by a liquid sporulation method. Supernatant from the spore culture of the liquid sporulation method may be reintroduced to the spores and used in forming a part of the biological indicator. The post-sporulation modification may improve the rapidity of the biological indicator by maintaining a portion of, or the complete, spore culture enzymatic profile. The post-sporulation modification also may improve resistance of the spores to sterilization by maintaining salts and/or the microbiological milieu which can protect spores from sterilization to a degree. Biological indicators may be produced that include the post-sporulation modified spores In accordance with an aspect of the present disclosure, a liquid sporulation method includes: preparing a liquid culture by adding bacterial cells to a sporulation broth; incubating the liquid culture; harvesting spores from the incubated liquid culture by separating the spores from a culture supernatant; suspending the harvested spores in an aqueous medium to form a spore suspension; and combining at least a portion of the culture supernatant with the spore suspension.

In some embodiments, the combining the at least a portion of the culture supernatant with the harvested spores suspended in the aqueous suspension includes: separating a portion of the aqueous medium from the spore suspension; and replacing the separated portion of the aqueous medium with a portion of the culture supernatant.

In some embodiments, a volume of the portion of the aqueous medium separated from the spore suspension is equal to a volume of the portion of the culture supernatant.

In some embodiments, the culture supernatant as recombined with the spore suspension is present in the range of 1%-75% by volume of the spore suspension.

In some embodiments, the culture supernatant as recombined with the spore suspension is present in the range of 1%-50% by volume of the spore suspension.

In some embodiments, the culture supernatant as recombined with the spore suspension is present in the range of 1%-25% by volume of the spore suspension.

In some embodiments, the method further includes diluting the culture supernatant prior to combination with the harvested spores suspended in the aqueous suspension.

In some embodiments, a concentration of enzymes dispersed in the culture supernatant after dilution is 80%-15% the concentration of the enzymes as dispersed in the culture supernatant prior to dilution.

In some embodiments, the method further includes concentrating the culture supernatant prior to combination with the harvested spores suspended in the aqueous suspension.

In some embodiments, a concentration of enzymes dispersed in the culture supernatant after concentration is 101%-200% the concentration of the enzymes as dispersed in the culture supernatant prior to concentration.

In some embodiments, the method further includes dialyzing the culture supernatant prior to combination with the spore suspension.

In some embodiments, the method further includes filtering the culture supernatant prior to combination with the spore suspension.

In some embodiments, the method further includes washing the harvested spores prior to combination with the culture supernatant.

In some embodiments, the method further includes heat shocking the harvested spores suspended in the aqueous suspension prior to combination with the culture supernatant.

In some embodiments, the bacterial cells include *Geobacillus stearothermophilus*.

In some embodiments, a volume of the liquid culture is in the range of 400 mL-600 mL.

In some embodiments, the sporulation broth includes one or more types of metal ions, one or more types of mineral ions, one or more buffers, and yeast extract dispersed in water.

In some embodiments, the one or more types of metal ions and the one or more types of mineral ions are from one or more dissociated inorganic salts provided in an amount falling in a range of 1 g/L to 20 g/L of the sporulation broth; the buffer is provided in an amount falling in a range of 1 g/L to 50 g/L of the sporulation broth; and the yeast extract is provided in an amount falling in a range of 0.5 g/L to 30 g/L of the sporulation broth.

In some embodiments, the one or more inorganic salts include one or more of ammonium sulfate ($NH_4SO_4$), magnesium sulfate ($MgSO_4$), manganese(II) sulfate ($Mn(II)SO_4$), iron(III) sulfate ($FeSO_4$), calcium sulfate ($CaSO_4$), potassium sulfate ($KSO_4$), and zinc sulfate ($ZnSO_4$).

In some embodiments, the one or more inorganic salts include one or more of potassium phosphate monobasic ($KH_2PO_4$), potassium phosphate dibasic ($K_2HPO_4$), iron phosphate ($Fe(III)PO_4$), calcium phosphate ($Ca(PO_4)_2$), tricalcium phosphate ($Ca_3(PO_4)_2$), magnesium ammonium phosphate ($MgNH_4PO_4$), sodium phosphate ($NaPO_4$), and zinc phosphate ($Zn(II)PO_4$).

In some embodiments, the one or more inorganic salts include one or more of calcium chloride ($CaCl_2$), ammonium chloride ($NH_4Cl$), magnesium chloride ($MgCl_2$), sodium chloride ($NaCl_2$), iron chloride ($FeCl_3$), manganese chloride ($MnCl_2$), potassium chloride ($KCl$), and zinc chloride ($ZnCl_2$).

In some embodiments, the buffer includes one or more of MOPS (3-(N-morpholino) propanesulfonic acid), citric acid ($C_6H_8O_7$), MES (2-(N-Morpholino)ethanesulfonic acid), BIS-TRIS ($C_8H_{19}NO_5$), PIPES (Piperazine-N,N'-bis(2-ethanesulfonic acid), MOPSO (3-morpholinopropanesulfonic acid), BES (N,N-bis[2-hydroxyethyl]-2-aminoethanesulfonic acid), TES (2-[[1,3-dihydroxy-2-(hydroxymethyl)propan-2-yl]amino]ethanesulfonic acid), HEPES (4-(2-hydroxyethyl)-1-piperazineethanesulfonic acid), and $KH_2PO_4$.

In some embodiments, the method further includes drying the combined culture supernatant and harvested spores suspended in the aqueous suspension on a carrier.

The following description and the annexed drawing set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

DETAILED DESCRIPTION

Figure 1:
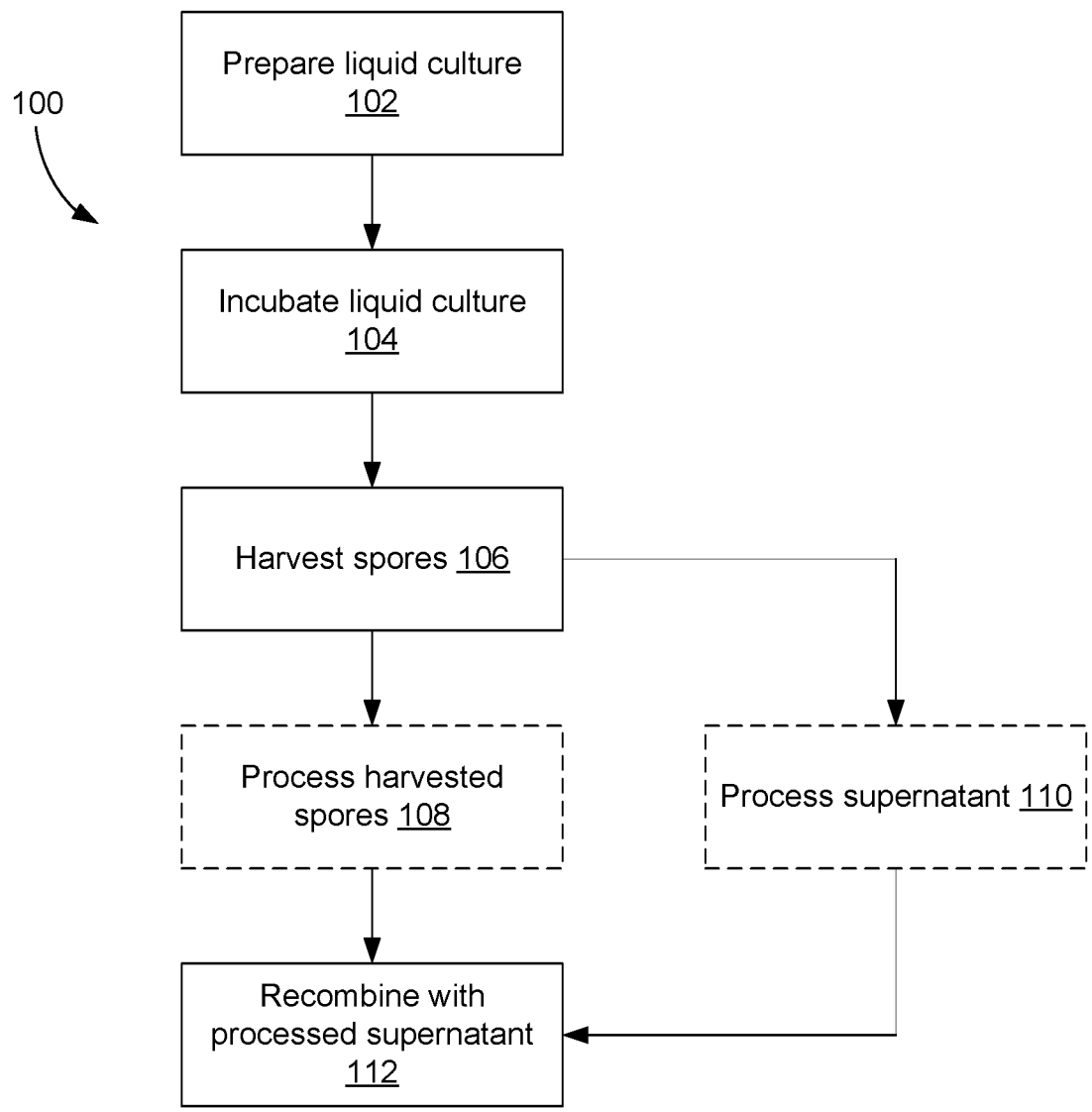
FIG. 1 is a flow chart showing an exemplary liquid sporulation method in connection with the present disclosure.
Figure 2:
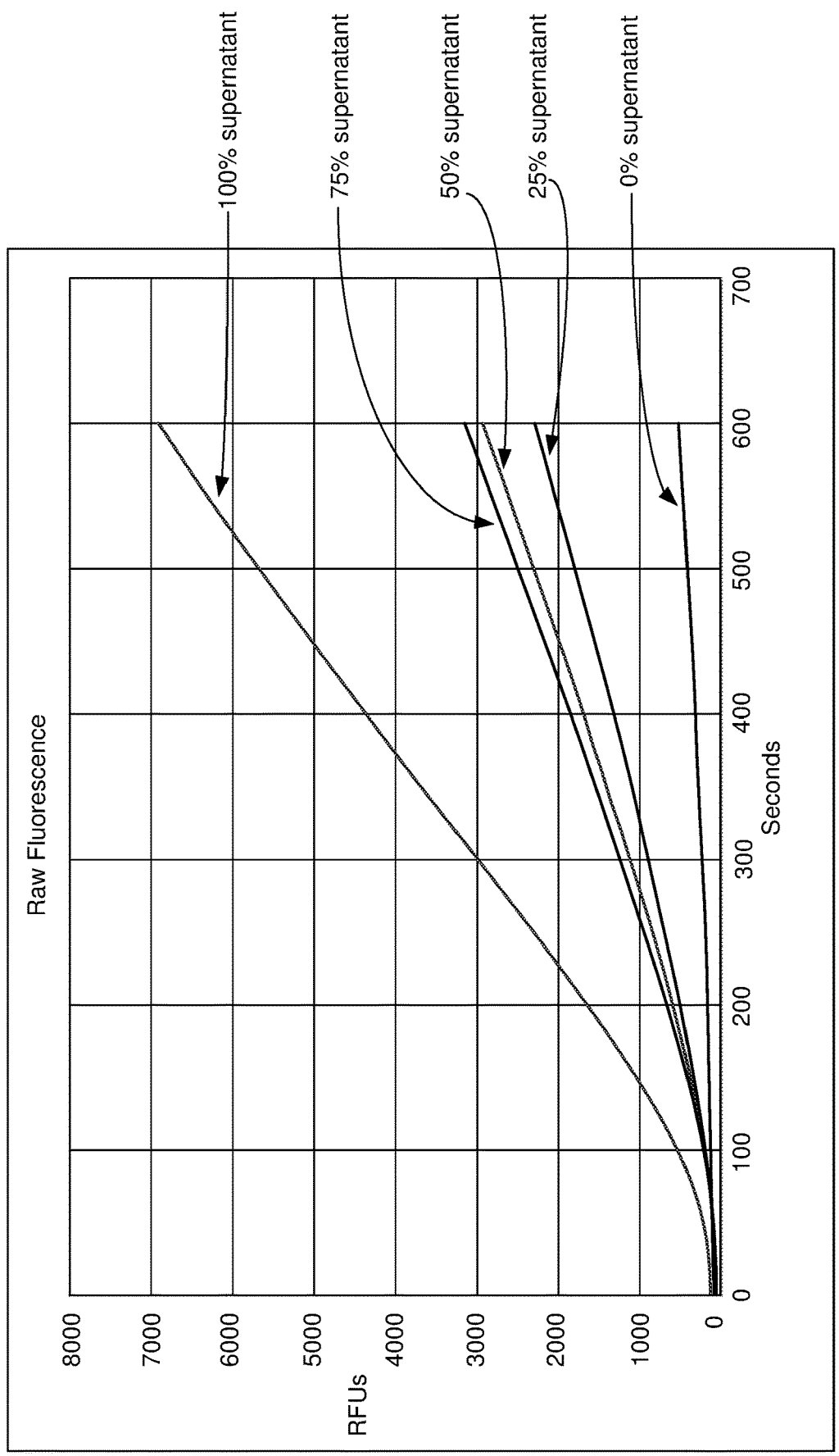
FIG. 2 is a graph showing the amount of detected fluorescence over time for spore samples produced in accordance with the present disclosure.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "biological indicator" refers to an article that can be used to determine the efficacy of a sterilization process. The biological indicator may include test microorganisms. The term "test microorganism" may refer to a microorganism that is more resistant to a sterilization process than the organisms intended for destruction during the sterilization process. In theory, if the test microorganisms were to die during the sterilization process, then all organisms intended for destruction during the sterilization process that were less resistant to the sterilization than the test microorganisms would also die. The test microorganisms may include a bacteria. The test microorganisms may include spores. The test microorganisms may include bacterial spores. The biological indicator may include the test microorganisms (e.g., bacteria, spores or bacterial spores) on a carrier. The biological indicator may include bacteria, the bacteria may be present within a defined space or deposited on a carrier. The biological indicator may include spores (e.g., bacterial spores), the spores may be present within a defined space or on a carrier. The biological indicator may include a spore strip.

The term "bacteria" refers to a domain of prokaryotic microorganisms.

The term "spore" refers to a non-reproductive dormant cell that may be adapted for dispersal and survival for extended periods of time under unfavorable conditions. Spores are highly resistant, dormant cell types. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore specific layers. The mother cell then disintegrates, releasing the mature dormant spore which requires neither nutrients, water nor air for survival and is protected against a variety of trauma, including extremes of temperature, radiation, and chemical assault.

The term "bacterial spore" refers to a spore produced by bacteria.

The term "carrier" refers to a support onto which test microorganisms or spores are deposited to form a biological indicator.

The term "killing" test microorganisms or spores refers to rendering test microorganisms or spores incapable of reproduction, metabolism and/or growth. The term "dead" test microorganisms or spores refers to spores which have been rendered incapable of reproduction, metabolism and/or growth. The test microorganisms or spores used with the biological indicator are selected from those that would be more resistant to a sterilization process for which they are intended to monitor than the organisms to be killed by the sterilization process. The killing of the test microorganisms or spores on the biological indicator during the sterilization process is indicative of a successful sterilization process.

The term "sterilization" may be used to refer to a process wherein there is a total absence of living test microorganisms remaining after the sterilization process has been completed. However, processes that are less rigorous than sterilization processes including, for example, disinfection, sanitization, decontamination, cleaning processes, and the like, may be of value in that they significantly reduce the total number of viable organisms and are taken into account with the present disclosure. Unless otherwise indicated, the term "sterilization" is used herein to refer to sterilization processes as well as less rigorous processes such as disinfection, sanitation, decontamination, cleaning, and the like.

The term "sterilant" refers to any medium or energy that can be used to sterilize a substrate (e.g., a medical device, the interior of a room, etc.). The sterilant may include a liquid or a gas. The sterilant may include vaporous hydrogen peroxide, steam, ethylene oxide, peracetic acid, ozone, or a combination of two or more thereof. The sterilant may include ultraviolet light or radiation. The radiation may include x-ray radiation, gamma radiation, or electron beam radiation.

Turning now to FIG. 1, an exemplary liquid sporulation method is shown at 100. At step 102, a liquid culture is prepared. The liquid culture may be prepared by adding bacterial cells to a sporulation broth. This sporulation broth may also be referred to as a "liquid sporulation medium" or "aqueous dispersion". The sporulation broth may be formulated to support high cell density growth as well as sporulation of the bacterial cells.

The sporulation broth includes one or more components (e.g., one or more types of metal ions, mineral ions, inorganic salts, buffers, carbon sources, peptones, amino acids, peptides, and/or yeast extract, and the like) dispersed in water. In some embodiments, the water is deionized water or distilled water.

The sporulation broth may include one or more types of metal ions and/or one or more types of mineral ions. The metal ions and mineral ions may be provided by the addition of one or more types of inorganic salts (such as metal salts and/or other types of inorganic salts) that may dissociate in the sporulation broth. Examples include sulfates such as ammonium sulfate ($NH_4SO_4$), magnesium sulfate ($MgSO_4$), manganese(II) sulfate ($Mn(II)SO_4$), iron(III) sulfate ($FeSO_4$), calcium sulfate ($CaSO_4$), potassium sulfate ($KSO_4$), and zinc sulfate ($ZnSO_4$), phosphates such as potassium phosphate monobasic ($KH_2PO_4$), potassium phosphate dibasic ($K_2HPO_4$), iron phosphate ($Fe(III)PO_4$), calcium phosphate ($Ca(PO_4)_2$), tricalcium phosphate ($Ca_3(PO_4)_2$), magnesium ammonium phosphate ($MgNH_4PO_4$), sodium phosphate ($NaPO_4$), and zinc phosphate ($Zn(II)PO_4$); chlorides such as calcium chloride ($CaCl_2$), ammonium chloride ($NH_4Cl$), magnesium chloride ($MgCl_2$), sodium chloride ($NaCl_2$), iron chloride ($FeCl_3$), manganese chloride ($MnCl_2$), potassium chloride ($KCl$), and zinc chloride ($ZnCl_2$); and combinations thereof.

In some embodiments, the total amount of inorganic salts added to the sporulation broth may fall in the range of 0.1 g/L to 20 g/L of the sporulation broth. In other embodiments, the total amount of inorganic salts added to the sporulation broth may fall in the range of 0.2 g/L to 10 g/L of the sporulation broth. In other embodiments, the total amount of inorganic salts added to the sporulation broth may fall in the range of 0.2 g/L to 5 g/L of the sporulation broth. In other embodiments, the total amount of inorganic salts added to the sporulation broth may fall in the range of 0.5 g/L to 1 g/L of the sporulation broth.

The sporulation broth may include one or more types of buffers. Exemplary buffers include MOPS (3-(N-morpholino) propanesulfonic acid), citric acid ($C_6H_8O_7$), MES (2-(N-Morpholino)ethanesulfonic acid), BIS-TRIS ($C_8H_{19}NO_5$), PIPES (Piperazine-N,N'-bis(2-ethanesulfonic acid), MOPSO (3-morpholinopropanesulfonic acid), BES (N,N-bis[2-hydroxyethyl]-2-aminoethanesulfonic acid), TES (2-[[1,3-dihydroxy-2-(hydroxymethyl)propan-2-yl]amino]ethanesulfonic acid), HEPES (4-(2-hydroxyethyl)-1-piperazineethanesulfonic acid), $KH_2PO_4$, and combinations thereof.

In some embodiments, the total amount of buffer added to the sporulation broth may fall in the range of 1 g/L to 50 g/L of the sporulation broth. In other embodiments, the total amount of buffer added to the sporulation broth may fall in the range of 5 g/L to 25 g/L of the sporulation broth. In other embodiments, the total amount of buffer added to the sporulation broth may fall in the range of 5 g/L to 15 g/L of the sporulation broth.

The sporulation broth may include one or more complex components. Exemplary complex components include trypticase peptone and yeast extract, which are components that have less defined characteristics. Trypticase peptone is the pancreatic digest of casein and may serve as a nitrogen source (peptones) for the cells, among other nutrients. Yeast extracts are concentrates from the water-soluble portion of autolyzed yeast cells and may provide vitamins, amino acids, and peptides, along with other nutrients, to the media formulation. Other exemplary complex components include components that provide one or more of peptones, amino acids, and/or peptides, such as one or more tryptones, casamino acids, meat extracts, and/or blood serums.

In some embodiments, the total amount of complex components added to the sporulation broth may fall in the range of 0.5 g/L to 40 g/L of the sporulation broth. In other embodiments, the total amount of complex components added to the sporulation broth may fall in the range of 5 g/L to 35 g/L of the sporulation broth. In other embodiments, the total amount of complex components added to the sporulation broth may fall in the range of 25 g/L to 35 g/L of the sporulation broth.

The sporulation broth may include one or more carbon sources. One exemplary carbon source is starch (and/or fragments thereof). Other exemplary carbon sources include saccharides such as glucose, sucrose, lactose, galactose, and/or maltose, glycogen (and/or fragments thereof), melezitose, and glycerols.

In some embodiments, the total amount of carbon source added to the sporulation broth may fall in the range of 0.5 g/L to 20 g/L of the sporulation culture. In other embodiments, the total amount of carbon source added to the sporulation broth may fall in the range of 1 g/L to 10 g/L of the sporulation broth. In other embodiments, the total amount of carbon source added to the sporulation broth may fall in the range of 2 g/L to 5 g/L of the sporulation broth. It is noted that in some embodiments, the sporulation broth does not include such carbon source.

Upon addition of the components to the water, the pH of the sporulation broth may be adjusted. In some embodiments, the pH of the sporulation broth may be adjusted using a pH adjusting compound such as potassium hydroxide (KOH) and/or sodium hydroxide (NaOH). As an example, the pH of the sporulation broth may be (or may be adjusted to be) in a range of 6.0-8.0. In other embodiments, the pH of the sporulation broth may be (or may be adjusted to be) in a range of 6.0-7.0. In other embodiments, the pH of the sporulation broth may be (or may be adjusted to be) about 6.5.

Table 1 provides an exemplary sporulation broth formulation including components dispersed in water.

TABLE 1

Exemplary sporulation broth formulation

| Component | Concentration (g/L) |
|---|---|
| MOPS (3-(N-morpholino) propanesulfonic acid) | 5.0-15.0 |
| Manganese(II) Sulfate (Mn(II)SO$_4$) | 0.1-0.75 |
| Calcium Chloride (CaCl$_2$) | 0.1-0.75 |
| Yeast Extract | 8-36 |

**pH adjusted to within the range of 6.0-7.0 with 1M NaOH

The bacterial cells may be vegetative cells selected from the genus *Geobacillus*, *Bacillus*, and/or *Clostridium*. In some embodiments, the bacterial cells are of a single species of bacteria. In other embodiments, the bacterial cells are a combination of two or more species and/or strains of bacteria.

Examples of bacteria belonging to the genus *Bacillus* include, but are not limited to, *Bacillus subtilis*, *Bacillus amyloliquefaciens*, *Bacillus pumilus*, *Bacillus lentus*, *Bacillus laterosporus*, *Bacillus alvei*, *Bacillus anthracis*, *Bacillus popilliae*, *Bacillus licheniformis*, *Bacillus coagulans*, *Bacillus subtilis globigii*, *Bacillus cereus*, *Bacillus circulans*, *Bacillus halodurans*, *Bacillus subtilis natto*, *Bacillus acidicola*, *Bacillus acidopullulyticus*, *Bacillus acidovorans*, *Bacillus aeolius*, *Bacillus aestuarii*, *Bacillus agaradhaerens*, *Bacillus akibai*, *Bacillus alcalinulnus*, *Bacillus alcalophilus*, *Bacillus algicola*, *Bacillus alkalitolerans*, *Bacillus alkalogaya*, *Bacillus alveayuensis*, *Bacillus amiliensis*, *Bacillus aminovorans*, *Bacillus aquimaris*, *Bacillus arbutinivorans*, *Bacillus arenosi*, *Bacillus areniciselenatis*, *Bacillus arsenicus*, *Bacillus arvi*, *Bacillus asahii*, *Bacillus atrophaeus*, *Bacillus axarguiensis*, *Bacillus azotoformans*, *Bacillus badius*, *Bacillus baekryungensis*, *Bacillus barbaricus*, *Bacillus bataviensis*, *Bacillus benzoevorans*, *Bacillus bogoriensis*, *Bacillus borophilicus*, *Bacillus borotolerans*, *Bacillus caldolyticus*, *Bacillus caldotenax*, *Bacillus caldovelox*, *Bacillus carboniphilus*, *Bacillus casamancensis*, *Bacillus catenulatus*, *Bacillus ceulosilyticus*, *Bacillus sphaericus*, *Bacillus thuringiensis*, and *Bacillus clausii*.

Examples of bacteria belonging to the genus *Clostridium* include, but are not limited to, *Clostridium sporogenes*, *Clostridium difficile*, and *Clostridium botulinum*.

Examples of bacteria belonging to the genus *Geobacillus* include, but are not limited to, *Geobacillus anatolicus*, *Geobacillus kaue*, *Geobacillus caldoproteolyticus*, *Geobacillus caldoxylosilyticus*, *Geobacillus debilis*, *Geobacillus gargensis*, *Geobacillus kaustophilus*, *Geobacillus stearothermophilus*, *Geobacillus thermocatenulatus*, *Geobacillus thermodenitrificans*, *Geobacillus thermoglucosidasius*, *Geobacillus thermoleovorans*, *Geobacillus uralicus*, *Geobacillus uzenensis*, and *Geobacillus vulcani*.

In some embodiments, the bacterial cells are vegetative cells selected from the genus *Geobacillus stearothermophilus*. The vegetative form of *Geobacillus stearothermophilus* is rod-shaped cells that produce one endospore per cell. The cell length ranges from 2.0-3.5 micrometers with a cell width ranging from 0.6-1.0 micrometers. In some embodiments, *Geobacillus stearothermophilus* American Type Culture Collection (ATCC) strain 7953 ("*Geobacillus stearothermophilus* 7953") is the bacteria strain combined with the sporulation culture to form the liquid culture.

The bacterial cells may be provided from any suitable source, such as an existing stock of bacteria. The bacterial cells may be provided in a solution/suspension, which may serve as an inoculum source (e.g., inoculum suspension) that is added to the sporulation broth.

In some embodiments, cryogenically frozen bacterial cells may be thawed and directly added to the aqueous dispersion. For example, one or more vials of the cryogenically frozen bacterial cells may be removed from cryostorage, warmed to room temperature (e.g., 21° C.), and the contents of the vial may be directly added to the broth. In some embodiments, a vial may have, for example, 5.0E7 to 1.0E9 cfu/mL bacterial cells dispersed in a solution such as glycerol. In some embodiments, at least 70% of the bacterial cells from the vial are vegetative cells.

In other embodiments, cryogenically frozen bacterial cells may be thawed and prepared for addition to the aqueous dispersion. For example, the one or more vials of the cryogenically frozen bacterial cells may be removed from cryostorage, warmed to room temperature (e.g., 21° C.), and then mixed on a vortex mixer. The contents of the one or more cryovials may then be centrifuged, and the bacteria may be separated from the resultant supernatant (e.g., by decanting) and resuspended in a medium such as water for injection (WFI) or an aliquot of the sporulation broth.

Of course, in other embodiments, the bacterial cells may not be cryogenically frozen and may be either directly added to the sporulation broth or prepared in a suspension prior to addition to the sporulation broth.

A predetermined volume containing the bacterial cells may be combined with a predetermined volume of the sporulation broth. In some embodiments, the culture is formed of a volume of liquid dispersion in a range of 400 mL-600 mL and a volume of the inoculum source (e.g., the suspension of bacterial cells as provided directly from the vial or the suspension of bacterial cells as prepared) in a range of 0.1 mL-2.5 mL. The culture may be an aliquot from a larger mixture having a ratio of liquid dispersion to inoculum such that the above ranges are satisfied.

At step 104, the liquid culture is incubated. During the incubation period, the bacterial cells of the liquid culture may grow and sporulate in the broth. During growth and sporulation, an enzymatic profile is also produced in the culture by the bacterial cells. The bacterial cells may generate enzymes both constitutively and/or as a result of being induced by environmental stimuli. Several types of enzyme may be formed. For example, the enzymatic profile may include one or more enzymes, such as beta-D-galactosidase, beta-glucosidase (e.g., gentiobiase, cellobiase, emulsin, elaterase, aryl-beta-glucosidase, beta-D-glucosidase, beta-glucoside glucohydrolase, arbutinase, amygdalinase, p-nitrophenyl beta-glucosidase, primeverosidase, amygdalase, linamarase, salicilinase, and/or beta-1,6-glucosidase), alpha-glucosidase (e.g., maltase, glucoinvertase, glucosidosucrase, maltase-glucoamylase, alpha-glucopyranosidase, glucosidoinvertase, alpha-D-glucosidase, alpha-glucoside hydrolase, alpha-1,4-glucosidase, and/or alpha-D-glucoside glucohydrolase), alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, or a mixture of two or more thereof. In some embodiments, at least one of the types of enzymes produced is alpha-glucosidase. The one or more enzymes may be produced by the bacterial cells as a normal component of their metabolism and may be present in the spore coat of the spore cells. These one or more enzymes, the activity of which may be detected using one or more enzyme substrates (e.g., in the validation of the performance of a sterilizer and/or sterilization cycle), may also be referred to as "indicator enzymes".

Other products that may be produced during growth/sporulation of the bacterial cells in the liquid culture include biological waste products such as acid and/or alcohols, fatty acids, digested proteins (e.g., peptides and/or amino acids), chelations of salts (e.g., calcium dipicolinate), polyamines, cell signaling molecules, nucleotides (e.g., RNA and DNA of differing types), and the like. In some embodiments, at least a portion of these other products may react with the sterilant used in a sterilization process (e.g., $H_2O_2$) and may dilute the sterilant to some degree briefly to protect the spore and enzyme and thus makes the spore and enzyme more resistant to degradation to some degree.

The liquid culture may be incubated in conditions to effect growth and sporulation of the bacteria. In some embodiments, the incubation temperature may be in the range of 35° C.-70° C. In other embodiment, the incubation temperature may be in the range of 40° C.-65° C. In other embodiment, the incubation temperature may be in the range of 55° C.-65° C.

The liquid culture may be shaken during incubation. In some embodiments, the rate of shaking may fall in the range of 50 rpm-400 rpm. In other embodiments, the rate of shaking may fall in the range of 100 rpm-300 rpm. In other embodiments, the rate of shaking may fall in the range of 150 rpm-250 rpm.

The vessel in which the liquid culture is incubated may also assist in stirring/agitation of the culture. For example, in some embodiments, the vessel in which the liquid culture is incubated may be a baffled Erlenmeyer flask.

The culture may be incubated for a predetermined period of time. As an example, the incubation period may be for a period of time falling in the range of 18 hours-48 hours. In another example, the incubation period may be for a period of time falling in the range of 18 hours-36 hours. As another example, the incubation period may be for 24 hours.

At step 106, the spores are harvested. In some embodiments, the liquid culture may be centrifuged, and the spores may be separated from the resultant culture supernatant (e.g., by decanting, biphasic separation, etc.). In some embodiments, he spores may be resuspended in a medium such as WFI, and these resuspended spores may also be referred to as a spore suspension. In other embodiments, the spores separated from the resultant culture supernatant (e.g., by decanting, biphasic separation, etc.) are not resuspended in a medium, and may be in the form of one or more spore pellets. The spore pellet(s) may instead subsequently be processed (optional step 108) and/or recombined with at least a portion of the culture supernatant (e.g., as described in step 112).

Optionally, at step 108, the harvested spores are processed. The spore suspension (or spore pellet(s)) may be subjected to one or more post-sporulation steps. In some embodiments, the spore suspension may be washed one or more times. A washing procedure may include the steps of resuspending the centrifuged spores in water, salt water, buffer, media, or other liquid, followed by centrifugation. Such a washing procedure may be repeated as necessary. The centrifuged spores may be resuspended in a medium. In some embodiments in which the spores are suspended in a medium at step 106, such medium may be utilized as part of the washing procedure.

In some embodiments, the spores may be subjected to a heat shock procedure. The heat shock procedure may be considered a modified heat shock procedure in that it uses an atypical heat shock profile. For example, while a typical heat shock procedure may be conducted in a temperature range of 95° C.-100° C. for a time period of about 15 minutes, the heat shock procedure conducted in the method of the present disclosure may be conducted at a lower temperature for a shorter amount of time. As an example, a water bath may be provided at a predetermined elevated temperature (e.g., 80° C.) and the vessel containing the spore suspension may be immersed in the water bath for a predetermined amount of time (e.g., 10 minutes), or for a given amount of time for the spore suspension to reach the predetermined temperature. The modified heat shock procedure may retain a functional enzyme profile of the spores while minimizing negative impact of spore resistance to steam sterilization. Enzymes that do not handle heat shocking as well as other enzymes may be preserved, and enzyme function may be preserved.

In other embodiments, the spore suspension (or spore pellet(s)) from step 106 is not subjected to washing or the heat shock procedure and step 108 is omitted. In other embodiments, the spore suspension (or spore pellet(s)) from step 106 is only subjected to washing. In other embodiments, the spore suspension from step 106 is only subjected to the heat shock procedure.

In some embodiments, the spores separated from the resultant culture supernatant (e.g., by decanting, biphasic separation, etc.) are resuspended and processed (e.g., washing and/or heat shock), and may subsequently be separated from the medium (e.g., by decanting, biphasic separation, etc.) to form the spore pellet(s) prior to being recombined with at least a portion of the culture supernatant (e.g., as described in step 112).

Optionally, at step 110, the culture supernatant separated from the spores during harvesting is processed. The culture supernatant includes the enzyme profile of the culture, and this enzyme profile may be used to modify the harvested spores. The processing may adjust the concentration and/or makeup of the supernatant, including the concentration of the enzymes produced by the bacterial cells during incubation, for addition to the harvested spores.

In some embodiments, the culture supernatant is diluted to a predetermined amount such that the components of the culture supernatant are reduced to fraction of their concentration in the decanted culture supernatant. The culture supernatant may be diluted with water or another suitable solution. In an example, the concentration of the components (e.g., the enzymes and/or other components dispersed in the aqueous solution) of the culture supernatant after dilution may be 80%-15% the concentration of the components of the culture supernatant prior to dilution. In another example, the concentration of the components (e.g., the enzymes and/or other components dispersed in the aqueous solution) of the culture supernatant after dilution may be 70%-15% the concentration of the components of the culture supernatant prior to dilution. In another example, the concentration of the components (e.g., the enzymes and/or other components dispersed in the aqueous solution) of the culture supernatant after dilution may be 60%-15% the concentration of the components of the culture supernatant prior to dilution. In another example, the concentration of the components (e.g., the enzymes and/or other components dispersed in the aqueous solution) of the culture supernatant after dilution may be 50%-15% the concentration of the components (e.g., the enzymes and/or other components dispersed in the aqueous solution) of the culture supernatant prior to dilution. In another example, the concentration of the components (e.g., the enzymes and/or other components dispersed in the aqueous solution) of the culture supernatant after dilution may be 40%-15% the concentration of the components of the culture supernatant prior to dilution. In another example, the concentration of the components (e.g., the enzymes and/or other components dispersed in the aqueous solution) of the culture supernatant after dilution may be 30%-15% the concentration of the components of the culture supernatant prior to dilution. In another example, the concentration of the components (e.g., the enzymes and/or other components dispersed in the aqueous solution) of the culture supernatant after dilution may be 30%-20% the concentration of the components of the culture supernatant prior to dilution.

In other embodiments, the concentration of the components (e.g., the enzymes and/or other components dispersed in the aqueous solution) of the culture supernatant are increased as compared with their concentration in the decanted culture supernatant. As an example, a portion of the culture supernatant may be evaporated (e.g., as part of a distillation process or other suitable process). Other exemplary processes for concentrating the culture supernatant may include reverse osmosis or dialysis in which liquid water is removed from the supernatant solution through a porous membrane concentrating the remaining constituents. In an example, the concentration of the components (e.g., the enzymes and/or other components dispersed in the aqueous solution) of the culture supernatant after concentration may be 101%-200% the concentration of the components of the culture supernatant prior to concentration. In another example, the concentration (e.g., the enzymes and/or other components dispersed in the aqueous solution) of the components of the culture supernatant after concentration may be 101%-150% the concentration of the components (e.g., the enzymes and/or other components dispersed in the aqueous solution) of the culture supernatant prior to concentration. In another example, the concentration of the components (e.g., the enzymes and/or other components dispersed in the aqueous solution) of the culture supernatant after concentration may be 101%-130% the concentration of the components (e.g., the enzymes and/or other components dispersed in the aqueous solution) of the culture supernatant prior to concentration. In another example, the concentration of the components (e.g., the enzymes and/or other components dispersed in the aqueous solution) of the culture supernatant after concentration may be 101%-125% the concentration of the components (e.g., the enzymes and/or other components dispersed in the aqueous solution) of the culture supernatant prior to concentration. In another example, the concentration of the components (e.g., the enzymes and/or other components dispersed in the aqueous solution) of the culture supernatant after concentration may be 105%-120% the concentration of the components of the culture supernatant prior to concentration.

In other embodiments, the culture supernatant may be processed to modify the makeup of the culture supernatant. The culture supernatant may be dialyzed against water or another suitable solution. In some embodiments, a salty buffer may be used to extract water from the supernatant while maintaining the larger enzyme. In other embodiments, one or more salts may be added to the culture supernatant to "salt-out" the enzymes included therein. Dialysis of the culture supernatant may provide the effect of increasing or decreasing the overall enzyme concentration of the culture supernatant.

In some embodiments, the processing of the culture supernatant may include filtering of the culture supernatant (e.g., to remove particulates and/or any other undesired components).

In some embodiments, the culture supernatant is not processed. Accordingly, as described below in connection with step 112, at least a portion of the culture supernatant may be recombined with the spore suspension (or spore pellet(s)), without the culture supernatant being subjected to processing.

At step 112, the spores are recombined with at least a portion of the culture supernatant. In some embodiments, the spores are in the form of the spore pellet(s), and the spore pellet(s) may be suspended therein (e.g., the medium in which the spores are dispersed in is 100% culture supernatant). In other embodiments, the spores are provided in the spore suspension and at least a portion of the culture supernatant is combined with at least a portion of the spore suspension. In some embodiments in which at least a portion of the culture supernatant is combined with at least a portion of the spore suspension, culture supernatant may be added to the existing volume of the spore suspension. In other embodiments, in which the at least a portion of the culture supernatant is combined with at least a portion of the spore suspension, a portion of the medium of the spore suspension is removed and culture suspension replaces the removed portion. For example, the spore suspension may be centrifuged, a portion of the medium of the spore suspension may be removed, and culture supernatant (e.g., a volume equal to that of the medium that was removed) may be added.

In some embodiments, the culture supernatant as recombined with the spores suspension is present in the range of 1%-99% by volume of the spore suspension. In other embodiments, the culture supernatant as recombined with the spore suspension is present in the range of 1%-75% by volume of the spore suspension. In other embodiments, the culture supernatant as recombined with the spore suspension is present in the range of 1%-60% by volume of the spore suspension. In other embodiments, the culture supernatant as recombined with the spore suspension is present in the range of 1%-50% by volume of the spore suspension. In other embodiments, the culture supernatant as recombined with the spore suspension is present in the range of 1%-40% by volume of the spore suspension. In other embodiments, the culture supernatant as recombined with the spore suspension is present in the range of 1%-30% by volume of the spore suspension. In other embodiments, the culture supernatant as recombined with the spore suspension is present in the range of 10%-25% by volume of the spore suspension.

The bacterial spore suspension may be used in the manufacture of a biological indicator. The biological indicator may comprise test microorganisms (e.g., spores) deposited on a carrier. The spore population for the biological indicator may be in the range from about 500,000 to about 4,000,000 spores, or from about 500,000 to about 2,500,000 spores, or from about 500,000 to about 1,500,000 spores, or from about 750,000 to about 1,200,000 spores or about $10^6$ cfu. The carrier may comprise a vial, strip, sheet or film of any material that does not dissolve or deteriorate during the sterilization processes. The carrier may comprise paper, e.g., cellulose, plastic, glass, ceramic, metal, or a combination of two or more thereof. The plastic may comprise a polyolefin, polypropylene, polystyrene, polycarbonate, polymethacrylate, polyacrylamide, polyimide, polyester, or a combination of two or more thereof.

In some embodiments, the carrier on which the test microorganisms (e.g., spores) are deposited may be a plastic or glass vial as in a self-contained biological indicator (SCBI). For example, the vial may be made of polypropylene. One example of a SCBI is the Celerity™ 20 STEAM SCBI supplied by STERIS Corporation. These SCBI's are characterized by spore populations of at least about $10^6$ Geobacillus stearothermophilus spores per test strip.

In other embodiments, the carrier on which the test microorganisms (e.g., spores) are deposited may be a spore test strip. One example of a spore test strip is the VERIFY@ Spore Test Strip for S40@ Sterilant Concentrate supplied by STERIS Corporation. These test strips are cellulose strips that are 0.6 cm wide, 3.8 cm long, and less than 0.1 cm thick. These test strips are characterized by spore populations of at least about $10^5$ Geobacillus stearothermophilus spores per test strip.

Use of the culture supernatant modified spores in a biological indicator may provide for the ability to adjust and provide enzymatic performance and/or resistance to sterilization in a predicted and/or calibrated manner. The post-sporulation modification of spores produced in liquid batches by including culture supernatant from the spore culture into the harvested spore suspension biological indicator may function as a mediator of fluorescent activity. Using the culture supernatant on the spores returns a functional enzyme profile to the spores. The added culture supernatant may in some embodiments increase the enzyme activity to above 100% of spore-derived activity. This may improve the rapidity of detection of fluorescence in a biological indicator. For example, in some embodiments, the time necessary to observe evidence of surviving indicator cells may be under one hour. In other embodiments, the time necessary to observe evidence of surviving indicator cells may be under 30 minutes. In other embodiments, the time necessary to observe evidence of surviving indicator cells may be under 10 minutes. In other embodiments, the time necessary to observe evidence of surviving indicator cells may be under 5 minutes.

The post-sporulation modification of spores produced in liquid batches by including culture supernatant from the spore culture into the harvested spore suspension biological indicator may also modulate spore resistance to sterilization medium (e.g., vaporous hydrogen peroxide). The salts and microbiological milieu of the culture supernatant can protect the spores from sterilization to a degree.

The biological indicator may be exposed to a sterilization medium during a sterilization process using any suitable procedure. This may be effected using a sterilization monitor containing the biological indicator. As such, the spores and enzymes from the supernatant may be exposed to a sterilization medium during the sterilization process, and may then be exposed to a recovery medium to determine whether the sterilization process was effective. The sterilization medium may include a gaseous or liquid sterilant, dry heat, radiation, and the like. In some embodiments, the sterilization medium is vaporous hydrogen peroxide (VHP).

The biological indicator along with the articles to be sterilized are exposed to the sterilization medium during the sterilization process. Upon completion of the sterilization process, the biological indicator is combined with the recovery medium that may include an enzyme substrate. The biological indicator is then incubated in the presence of the recovery medium including enzyme substrate for a desired period of time and examined to determine whether the sterilization process was effective.

The recovery medium may include an aqueous medium or aqueous solution that provides for germination and/or metabolism of organisms as required. The pH of the recovery medium may be in the range from about 5 to about 9.5, or about 6.5 to about 7.5, or about 7.0. In some embodiments, the recovery medium includes lysogeny broth (LB). An example of an LB that may be used is set forth in Table 2:

TABLE 2

Exemplary lysogeny broth

| Component | |
|---|---|
| Deionized water | 800 mL |
| NaCl | 10 g/L |
| Tryptone | 10 g/L |
| Yeast Extract | 5 g/L |

**deionized water to provide final volume of 1 liter
**pH adjusted to within the range of 6.0-7.0 with NaOH The concentration of enzyme substrate in the recovery medium may be dependent upon the identity of the enzyme substrate and the enzyme, the amount of enzyme-modified product that must be generated to be detectable, either visually or by instrument, and the amount of time required to determine whether indictor enzyme is present. The amount of enzyme substrate that may be sufficient may be the amount needed to react with any enzyme that may be present after the sterilization has been completed such that an enzyme-modified product at a molar concentration of at least about $10^{-15}$ molar may be produced within a period of up to about 4 hours, or a molar concentration of at least about $10^{-8}$ molar within a period up to about 2 hours.

A viable enzyme acts upon an enzyme substrate to form an enzyme-modified product. The enzyme-modified product may comprise a luminescent, fluorescent or colored material that can be detected. In an example, the presence of this enzyme can be detected by reading fluorescence produced by the breakdown of a non-fluorescent enzyme substrate. Breakdown of the enzyme substrate can be an early detection alternative to waiting for a visual pH color change to indicate a failed sterilization process. Neither growth nor metabolism is required for the fluorometric signal. This results in a reduction in the time required to observe a failure in the sterilization process.

The enzyme substrate may comprise a substance or mixture of substances which when acted upon by the enzyme is converted into an enzyme-modified product. In general, the enzyme-modified product may comprise a luminescent, fluorescent, or colored material. Alternatively, the enzyme substrate may comprise one or more compounds which when acted upon by the enzyme, may yield a product which reacts with an additional compound or composition to yield a luminescent, fluorescent, or colored material.

There are two basic types of enzyme substrates that may be used for the detection of specific enzymes. The first type of enzyme substrate may be either fluorogenic or chromogenic, and may be given a chemical formula such as, AB. When acted upon by the enzyme, AB, may break down to A+B. B, for example, may be either fluorescent or colored. In one embodiment, two B compounds may react together to produce the fluorescent or colored signal. A specific example of a fluorogenic substrate of this type may be 4-methylumbelliferyl phosphate. In the presence of the enzyme phosphatase, the substrate may be broken down into 4-methylumbelliferone and phosphate. Other fluorogenic substrates of this type may include the derivatives of 4-methylumbelliferyl, 7-amido-4-methylcoumarin, indoxyl and fluorescein. An example of a chromogenic substrate of this type may be 5-bromo-4-chloro-3-indolyl phosphate. In the presence of phosphatase, the substrate may be broken down into indigo blue and phosphate. Other chromogenic substrates of this type may include derivatives of 5-bromo-4-chloro-3-indolyl, nitrophenol and phenolphthalein.

The second type of enzyme substrate may be given by the chemical formula CD, for example, which may be converted by a specific enzyme to C+D. However, neither C nor D may be fluorescent or colored, but D may be capable of being further reacted with compound Z to give a fluorescent or colored compound, thus indicating enzyme activity. A specific fluorogenic example of this type may be the amino acid lysine. In the presence of the enzyme lysine decarboxylase, lysine may lose a molecule of $CO_2$. The remaining part of the lysine may then be called cadaverine, which is strongly basic. A basic indicator such as 4-methylumbelliferone may be incorporated and may be fluoresce in the presence of a strong base. A chromogenic substrate of this type may be 2-naphthyl phosphate. The enzyme phosphatase, may react with the enzyme substrate to yield beta-naphthol. The liberated beta-naphthol may react with a chromogenic reagent containing 1-diazo-4-benzoylamino-2, 5-diethoxybenzene to produce a violet color.

The enzyme substrate may comprise a fluorogenic compound, defined herein as a compound capable of being enzymatically modified, e.g., by hydrolysis, to provide a derivative fluorophore which has an appreciably modified or increased fluorescence.

The fluorogenic compounds may in themselves be either non-fluorescent or meta-fluorescent (i.e., fluorescent in a distinctly different way, e.g., either by color or intensity, than the corresponding enzyme-modified products) and appropriate wavelengths of excitation and detection, may be used to separate the fluorescence signal developed by the enzyme modification from any other fluorescence that may be present.

A number of enzyme substrates for enzymes of diverse origins may be used. These may include fluorogenic 4-methylumbelliferyl derivatives (hydrolyzable to 4-methylumbelliferone); derivatives of 7-amido-4-methyl-coumarin; diacetylfluorescein derivatives; and fluorescamine.

Where the enzyme whose activity is to be detected is alpha-D-glucosidase, chymotrypsin or fatty acid esterase, a fluorogenic enzyme substrate that may be used may be 4-methylumbelliferyl-alpha-D-glucoside, 7-glutarylphenyl-alanine-7-amido-4-methyl coumarin, or 4-methylumbelliferyl heptanoate, respectively. Where the enzyme whose activity is to be detected is alpha-L-arabinofuranosidase, a fluorogenic enzyme substrate that may be used may be 4-methylumbelliferyl-alpha-L-arabinofuranoside. Where the enzyme whose activity is to be detected is beta-D-glucosidase, a fluorogenic enzyme substrate that may be used may be 4-methylumbelliferyl-beta-D-glucoside.

An enzyme substrate that may be used may be a chromogenic compound capable of being enzymatically modified to give a derivative chromophore, or a product which reacts with another compound to give a derivative chromophore, which chromophore has a different or more intense color. The chromogenic compounds may be non-colored or colored in a distinctly different way, e.g., either by color or intensity, than the corresponding enzyme-modified products. Appropriate wavelengths of excitation and detection, in manners well known to users of colorometric instrumentation, may be used to separate the colored signal developed by the enzyme modification from any other color that may be present.

Chromogenic compounds that may be used as enzyme substrates may include 5-bromo-4-chloro-3-indolyl derivatives; nitrophenyl derivatives; indoxyl derivatives; and phenolphthalein derivatives. The chromogenic enzyme substrate may react directly with an appropriate enzyme to produce a chromophore.

Additional enzyme substrates containing 1-naphthyl, 2-naphthyl and Napthyl-AS-BI derivatives may be employed if the derivative enzyme modified product is further reacted with a chromogenic reagent, such as diazotized dyes, e.g., 1-diazo-4-benzoylamino-2, 5-diethoxybenzene, 1-diazo-4-benzoylamino-2, 5-diethoxybenzene, p-diazo-2,5-diethoxy-N-benzoyalanine, 4-chloro-2-methylbenzene diazonium chloride, and o-aminoazotoluene diazonium salt, to produce a chromophore.

Where the enzyme whose activity is to be detected is alpha-D-glucosidase, the enzyme substrate may be p-nitrophenyl-alpha-glucopyranoside. Where the enzyme whose activity is to be detected is alpha-L-arabinofuranosidase, the enzyme substrate that may be used may be p-nitrophenyl-alpha-L-arabinofuranoside. Where the enzyme whose activity is to be detected is β-galactosidase, the enzyme substrate may be 5-bromo-4-chloro-3-indolyl-β-D-galactopyranoside or 4-methylumbelliferone-β-D-galactopyranoside.

The enzyme substrate that may be used may depend upon the identity of the enzyme whose activity is under study. Table 3 sets forth a list of a number of enzyme substrates, and corresponding enzymes which may react with the enzyme substrate to produce a product having appreciably modified or increased fluorescence or color.

TABLE 3

Exemplary enzyme substrates and corresponding enzymes

| Enzyme Substrate | Enzyme |
| --- | --- |
| 4-Methylumbelliferyl acetate | Esterase |
| 4-Methylumbelliferyl butyrate | Esterase |
| 4-Methylumbelliferyl elaidate | Lipase |
| 4-Methylumbelliferyl-β-D-galactopyranoside | β-D-Galactosidase |
| 4-Methylumbelliferyl-α-D-galactopyranoside | α-D-Galactosidase |
| 4-Methylumbelliferyl-α-D-glucopyranoside | α-D-Glucosidase |
| 4-Methylumbelliferyl-β-D-glucopyranoside | β-D-Glucosidase |
| 4-Methylumbelliferyl heptanoate | Esterase |
| 4-Methylumbelliferyl oleate | Lipase |
| 4-Methylumbelliferyl phosphate | Acid or Alkaline Phosphatase |
| 4-Methylumbelliferyl propionate | Esterase |
| 4-Methylumbelliferyl-β-D-galactoside | β-D-Galactosidase |
| 4-Methylumbelliferyl-β-D-glucoside | β-D-Glucosidase |
| 4-Methylumbelliferyl-α-D-glucoside | α-D-Glucosidase |
| 4-Methylumbelliferyl-α-L-arabinofuranoside | α-L-Arabinofuranosidase |
| L-Leucine-7-amido-4-methylcoumarin | Leucine aminopeptidase |
| 7-glutaryl-phenylalanine-7-amido-4-methylcoumarin | Chymotrypsin |
| D-Melibiose | α-D-Galactosidase |
| p-Nitrophenyl phosphate | Alkaline or Acid phosphatase |
| p-Nitrophenyl acetate | Lipase |
| o-Nitrophenyl-β-D-galactopyranoside | β-D-Galactosidase |
| p-Nitrophenyl-α-D-galactopyranoside | α-D-Galactosidase |
| o-Nitrophenyl-β-D-glucopyranoside | β-D-Glucosidase |
| p-Nitrophenyl-α-D-glucopyranoside | α-D-Glucosidase |
| p-Nitrophenyl-β-D-glucuronide | β-D-Glucuronidase |
| p-Nitrophenyl-α-L-arabinofuranoside | α-L-Arabinofuranosidase |
| p-Nitrophenyl laurate | Esterase |
| p-Nitrophenyl myristate | Esterase |
| p-Nitrophenyl palmitate | Esterase |
| p-Nitrophenyl phosphate diNa salt | Alkaline Phosphatase |
| Phenolphthalein dibutyrate | Esterase |
| Phenolphthalein diphosphate | Acid or Alkaline phosphatase |
| Phenolphthalein diphosphate pentaNa salt | Acid or Alkaline phosphatase |
| Phenolphthalein-β-D-glucuronide Na salt | β-D-Glucuronidase |
| Phenolphthalein-β-D-glucuronide | β-D-Glucuronidase |
| L-Phenylalanine ethylester HCl | Chymotrypsin |
| Phenyl-β-D-galactopyranoside | β-D-Galactosidase |
| Phenyl-β-D-glucuronide | β-D-Glucuronidase |
| Phenyl-β-D-glucopyranoside | β-D-Glucosidase |
| Phenyl-β-D-glucuronide | β-D-Glucuronidase |
| Phenyl-α-D-glucoside | α-D-Glucosidase |
| Sodium β-glycerophosphate | Acid or Alkaline phosphatase |
| Sodium 1-naphthyl phosphate | Acid or Alkaline phosphatase |
| Sodium 2-naphthyl phosphate | Acid or Alkaline phosphatase |
| 2-Naphthyl-butyrate | Esterase |
| β-Naphthyl acetate | Lipase |
| 6-Br-2-naphthyl-β-D-glucoside | β-D-Glucosidase |
| L-Leucyl-2-naphthylamide aminopeptidase | Leucine |
| L-Valyl-2-naphthylamide aminopeptidase | Valine |
| N-glutaryl-phenylalanine-2-naphthylamine | Chymotrypsin |
| Naphthyl-AS-BI-phosphate | Phosphohydralase |
| Indoxyl acetate | Lipase |
| N-Methylindoxyl acetate | Lipase |
| N-Methylindoxyl myristate | Lipase |
| 5-Bromoindoxyl acetate | Lipase |

TABLE 3-continued

Exemplary enzyme substrates and corresponding enzymes

| Enzyme Substrate | Enzyme |
| --- | --- |
| 3-Indoxyl phosphate | Acid or Alkaline phosphatase |
| Indoxyl-β-D-glucoside | β-D-Glucosidase |
| 5-Br-4-Cl-3-Indolyl acetate | Lipase |
| 5-Br-4-Cl-3-Indolyl phosphate | Alkaline or Acid phosphatase |
| 5-Br-4-Cl-3-Indolyl-β-D-glucuronic acid | β-D-Glucuronidase |
| Diacetylfluorescein | Lipase/esterase |

The sterilization monitor may be a self-contained sterilization monitor comprising a container with two separate compartments. One of the compartments may contain the biological indicator. The other compartment may contain the recovery medium. In use, the sterilization monitor and the articles to be sterilized are exposed to the sterilization medium. Following sterilization, the sterilization monitor is activated so that the biological indicator comes into contact with the recovery medium (e.g., including the enzyme substrate) sufficiently to determine whether the sterilization process is effective.

The activated sterilization monitor may be incubated. Incubation may be continued for a period of time and under conditions sufficient to liberate a detectable amount of the enzyme, assuming any of the biological indicator remains functional. In general, the amount of enzyme which may be detectable may be as low as about $1 \times 10^{-15}$ molar. The incubation conditions may be sufficient to generate at least about $1 \times 10^{-8}$ molar of enzyme, or from about $1 \times 10^{-6}$ to about $1 \times 10^{-5}$ molar of enzyme. The incubation time and temperature needed to produce a detectable amount of enzyme may depend upon the identity of the enzyme, and the concentration of the enzyme in the growth medium. The incubation temperature may be in the range from about 20° C. to about 70° C. The incubation time may be in the range up to about 4 hours, or in the range from about 0.01 to about 4 hours, or in the range from about 0.01 to about 3 hours, or in the range from about 0.01 to about 2 hours, or in the range from about 0.01 to about 1 hour. The enzyme acts upon the enzyme substrate to form an enzyme-modified product which can be detected. Detection can be achieved within a period of time of up to about 4 hours, or about 0.01 to about 4 hours, or about 0.01 to about 3 hours, or about 0.01 to about 2 hours, or about 0.01 to about 1 hour, or about 0.01 to about 0.7 hour, or about 0.01 to about 0.5 hour.

Generally applicable methods for detecting the enzyme-modified product may include photometric, potentiometric, gravimetric, calorimetric, conductometric, or amperometric techniques. Fluorometric or spectrophotometric methods may be used.

Example 1—Preparation of Post-Sporulation Modified Spore Suspension

Sporulation broth is prepared that includes the formulation set forth in Table 4. The identified components are added to 800 mL deionized water and then the volume is increased to 1 L such that the components are provided at the listed concentrations. 500 mL of the sporulation broth is transferred to a 2 L baffled Erlenmeyer flask.

TABLE 4

Sporulation broth formulation

| Component | Concentration (g/L) |
| --- | --- |
| MOPS (3-(N-morpholino) propanesulfonic acid) | 10 |
| Manganese(II) Sulfate (Mn(II)SO$_4$) | 0.3 |
| Calcium Chloride (CaCl$_2$) | 0.3 |
| Yeast Extract | 28 |

**pH adjusted to 6.5 with 1M NaOH

A cryovial containing a 1 mL of *Geobacillus stearothermophilus* 7953 in cryogenic media is removed from cryostorage, allowed to warm to room temperature (21° C.), and then mixed on a vortex mixer. 200 μL of the contents of the cryovial are then added directly to the 500 mL aliquot of the sporulation broth to create a liquid culture.

The baffled Erlenmeyer flask is incubated at 57° C. while being shaken at 200 rpm for 24 hours. After the 24-hour incubation, the spores are harvested from the culture. The culture is transferred to a centrifuge tube, centrifuged for 10 minutes at 4700 rpm, the culture supernatant is decanted, and the spores are resuspended in equal volume WFI. The resuspended spores are heat shocked for 10 minutes at 80° C.

A portion of the culture supernatant is combined with the spore suspension. More specifically, the spore suspension is centrifuged and 25% of the volume is removed as supernatant via decanting. This 25% volume is replaced with an equal volume of the culture supernatant.

Example 2—Preparation of Post-Sporulation Modified Spore Suspension

A spore suspension is produced in accordance with the process of Example 1, except that the culture supernatant is combined with the spore suspension in a different amount. The spore suspension is centrifuged and 50% of the volume is removed as supernatant via decanting. This 50% volume is replaced with an equal volume of the culture supernatant.

Example 3—Preparation of Post-Sporulation Modified Spore Suspension

A spore suspension is produced in accordance with the process of Example 1, except that the culture supernatant is combined with the spore suspension in a different amount. The spore suspension is centrifuged and 75% of the volume is removed as supernatant via decanting. This 75% volume is replaced with an equal volume of the culture supernatant.

Example 4—Preparation of Post-Sporulation Modified Spore Suspension

A spore suspension is produced in accordance with the process of Example 1, except that the medium of the spore suspension is removed and replaced by culture supernatant. Accordingly, the medium in which the spores are dispersed is 100% culture supernatant.

Example 5—Preparation of Control Spore Suspension

A spore suspension is produced in accordance with the process of Example 1, except that the culture supernatant is not combined with the spore suspension. Accordingly, the medium of the spore suspension is 100% water.

Example 6—Preparation and Testing of Carriers Having Post-Sporulation Modified Spores Thereon Aliquots of the spore suspensions produced in Examples 1-5 are transferred to respective carriers and dried. For each spore suspension, 20 μL of spore suspension transferred to a BI vial and dried under ambient conditions (21° C. and 1 atm). Five samples are prepared for each concentration.

The samples are subjected to a 2.5 g VHP BIER cycle for different respective durations and analyzed to determine survivor percent of the spores. Table 5 shows the results of the testing

TABLE 5

| Survivor percentage | | | | | | |
|---|---|---|---|---|---|---|
| Example | Supernatant % | Unexposed | 60 sec VHP | 90 sec VHP | 120 sec VHP | 150 sec VHP |
| 5 | 0% | 100% | 60% | 0% | 0% | 0% |
| 1 | 25% Supernatant | 100% | 70% | 20% | 10% | 10% |
| 2 | 50% Supernatant | 100% | 100% | 80% | 50% | 20% |
| 3 | 75% Supernatant | 100% | 100% | 90% | 90% | 40% |
| 4 | 100% Supernatant | 100% | 100% | 100% | 100% | 80% |

Example 7—Preparation and Testing of Carriers Having Post-Sporulation Modified Spores Thereon Aliquots of the spore suspensions produced in Examples 1-5 are transferred to respective carriers and dried. For each spore suspension, 20 μL of spore suspension transferred to a BI vial and dried under ambient conditions (21° C. and 1 atm). The samples are not subjected to a sterilization process and therefore considered to be positive controls.

The samples are brought into contact with a recovery medium including enzyme substrate and the fluorescence of the samples are monitored. FIG. 2 is a graph showing the amount of detected fluorescence over time.

While the present disclosure has been explained in relation to various embodiments, it is to be understood that various modifications thereof will become apparent to those skilled in the art upon reading the specification. Therefore, it is to be understood that the disclosure described herein includes any such modifications that may fall within the scope of the appended claims.

The invention claimed is:

1. A liquid sporulation method, comprising:

preparing a liquid culture by adding bacterial cells to a sporulation broth;

incubating the liquid culture;

harvesting spores from the incubated liquid culture by separating the spores from a culture supernatant;

suspending the harvested spores in an aqueous medium to form a spore suspension; and combining at least a portion of the culture supernatant with the spore suspension, wherein the culture supernatant as recombined with the spore suspension is present in the range of 1%-99% by volume of the spore suspension.

2. The method of claim 1, wherein the combining the at least a portion of the culture supernatant with the harvested spores suspended in the aqueous suspension comprises:

separating a portion of the aqueous medium from the spore suspension; and replacing the separated portion of the aqueous medium with a portion of the culture supernatant.

3. The method of claim 2, wherein a volume of the portion of the aqueous medium separated from the spore suspension is equal to a volume of the portion of the culture supernatant.

4. The method of claim 1, wherein the culture supernatant as recombined with the spore suspension is present in the range of 1%-75% by volume of the spore suspension.

5. The method of claim 1, wherein the culture supernatant as recombined with the spore suspension is present in the range of 1%-50% by volume of the spore suspension.

6. The method of claim 1, wherein the culture supernatant as recombined with the spore suspension is present in the range of 1%-25% by volume of the spore suspension.

7. The method of claim 1, further comprising diluting the culture supernatant prior to combination with the harvested spores suspended in the aqueous suspension.

8. The method of claim 7, wherein a concentration of enzymes dispersed in the culture supernatant after dilution is 80%-15% the concentration of the enzymes as dispersed in the culture supernatant prior to dilution.

9. The method of claim 1, further comprising concentrating the culture supernatant prior to combination with the harvested spores suspended in the aqueous suspension.

10. The method of claim 9, wherein a concentration of enzymes dispersed in the culture supernatant after concentration is 101%-200% the concentration of the enzymes as dispersed in the culture supernatant prior to concentration.

11. The method of claim 1, further comprising dialyzing the culture supernatant prior to combination with the spore suspension.

12. The method of claim 1, further comprising filtering the culture supernatant prior to combination with the spore suspension.

13. The method of claim 1, further comprising washing the harvested spores prior to combination with the culture supernatant.

14. The method of claim 1, further comprising heat shocking the harvested spores suspended in the aqueous suspension prior to combination with the culture supernatant.

15. The method of claim 1, wherein the bacterial cells comprise *Geobacillus stearothermophilus*.

16. The method of claim 1, wherein a volume of the liquid culture is in the range of 400 mL-600 mL.

17. The method of claim 1, wherein the sporulation broth comprises one or more types of metal ions, one or more types of mineral ions, one or more buffers, and yeast extract dispersed in water.

18. The method of claim 17, wherein:
the one or more types of metal ions and the one or more types of mineral ions are from one or more dissociated inorganic salts provided in an amount falling in a range of 1 g/L to 20 g/L of the sporulation broth;
the buffer is provided in an amount falling in a range of 1 g/L to 50 g/L of the sporulation broth; and
the yeast extract is provided in an amount falling in a range of 0.5 g/L to 30 g/L of the sporulation broth.

19. The method of claim 18, wherein the one or more inorganic salts comprise one or more of ammonium sulfate ($NH_4SO_4$), magnesium sulfate ($MgSO_4$), manganese(II) sulfate ($Mn(II)SO_4$), iron(III) sulfate ($FeSO_4$), calcium sulfate ($CaSO_4$), potassium sulfate ($KSO_4$), and zinc sulfate ($ZnSO_4$).

20. The method of claim 18, wherein the one or more inorganic salts comprise one or more of potassium phosphate monobasic ($KH_2PO_4$), potassium phosphate dibasic ($K_2HPO_4$), iron phosphate ($Fe(III)PO_4$), calcium phosphate ($Ca(PO_4)_2$), tricalcium phosphate ($Ca_3(PO_4)_2$), magnesium ammonium phosphate ($MgNH_4PO_4$), sodium phosphate ($NaPO_4$), and zinc phosphate ($Zn(II)PO_4$).

21. The method of claim 18, wherein the one or more inorganic salts comprise one or more of c alcium chloride ($CaCl_2$), ammonium chloride ($NH_4C$), magnesium chloride ($MgCl_2$), sodium chloride $NaCl_2$), iron chloride ($FeCl_3$), (manganese chloride ($MnCl_2$), potassium chloride (KCl), and zinc chloride ($ZnCl_2$).

22. The method of claim 18, wherein the buffer comprises one or more of MOPS (3-(N-morpholino) propanesulfonic acid), citric acid ($C_6H_8O_7$), MES (2-(N-Morpholino)ethanesulfonic acid), BIS-TRIS ($C_8H_{19}NO_5$), PIPES (Piperazine-N,N'-bis(2-ethanesulfonic acid), MOPSO (3-morpholinopropanesulfonic acid), BES (N,N-bis[2-hydroxyethyl]-2-aminoethanesulfonic acid), TES (2-[[1,3-dihydroxy-2-(hydroxymethyl)propan-2-yl]amino]ethanesulfonic acid), HEPES (4-(2-hydroxyethyl)-1-piperazineethanesulfonic acid), and $KH_2PO_4$.

23. The method of claim 1, further comprising drying the combined culture supernatant and harvested spores suspended in the aqueous suspension on a carrier.

* * * * *